United States Patent
Perlitz et al.

[11] Patent Number: 6,096,769
[45] Date of Patent: Aug. 1, 2000

[54] FUNGICIDAL CO-FORMULATION

[75] Inventors: Michael Perlitz, Ingelheim; Friedrich Schmidt, Engelstadt; Annerose Edith Elise Rehnig, Ingelheim; Ewald Gerhard Sieverding, St. Johann, all of Germany; Christopher William Horsler, Southampton, United Kingdom

[73] Assignee: American Cyanamid Company, Madison, N.J.

[21] Appl. No.: 09/063,199

[22] Filed: Apr. 20, 1998

[51] Int. Cl.$^7$ ..................................... A01N 43/82
[52] U.S. Cl. ..................... 514/361; 514/362; 514/363; 514/364
[58] Field of Search ..................... 514/361, 362, 514/363, 364

[56] References Cited

U.S. PATENT DOCUMENTS

| | | | |
|---|---|---|---|
| 4,938,792 | 7/1990 | Kumarzawa et al. | 71/92 |
| 5,393,770 | 2/1995 | Grayson | 514/383 |
| 5,438,066 | 8/1995 | Matthews | 514/361 |
| 5,668,160 | 9/1997 | Clough et al. | 514/364 |

*Primary Examiner*—Jose' G. Dees
*Assistant Examiner*—Alton Pryor
*Attorney, Agent, or Firm*—Barbara L. Renda

[57] ABSTRACT

The invention relates a concentrated liquid fungicidal composition comprising a fungicidally acceptable carrier and/or surface active agent and (a) at least one compound of formula I,

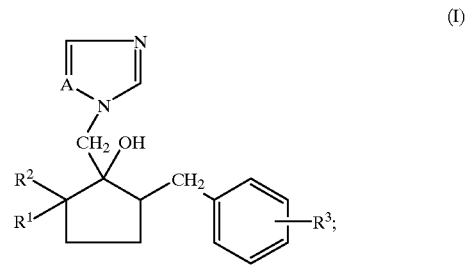

(b) one or more additional fungicidal active ingredients, which exist as a suspension of fire particles;

(c) a solubilizing agent; and (d) a dispersing agent, which has the capability to adsorb irreversibly on the surfaces of hydrophobic particles suspended in water or polar organic solvents.

15 Claims, No Drawings

FUNGICIDAL CO-FORMULATION

BACKGROUND OF THE INVENTION

The present invention relates to a concentrated liquid fungicidal composition comprising a fungicidally acceptable carrier and (a) at least one azole derivative of formula I

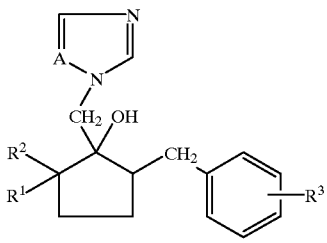

(I)

in which

R$^1$ and R$^2$ each independently represent hydrogen atom or an optionally substituted alkyl alkenyl, alkynyl or alkadienyl group;

R$^3$ represents a halogen atom or an optionally substituted alkyl, alkenyl, alkynyl, alkadienyl, alkoxy or aryl group; and A represents a nitrogen atom or a CH group;

or one of the salts or addition products thereof; which exists in dissolved form; and (b) one or more additional fungicidal active ingredients, which exist as a suspension of fine particles.

The fungicidal compounds of formula I to be used according to the present invention are known from U.S. Pat. No. 4,938,792.

U.S. Pat. No. 5,393,770 discloses concentrated fungicidal compositions comprising compounds of formula I and solubilizing agents and suggests the addition of different fungicidally active ingredients, including dithianon, fenpropimorph and chlorothalonil, to the tank mix of a compound of formula I to combat diseases caused by *Erysiphe graminis fsp tritici*.

However, there have been no concentrated liquid co-formulations comprising a compound of formula I and a second fungicidal active ingredient. In the preparation of suitable co-formulations comprising a compound of formula I, a solubilizing agent and a second fungicidally active ingredient, the problem poses itself that, because of the interaction between the second active ingredient and the solubilizing agent used, a homogeneous or stable homogeneous formulation cannot be obtained. However, a combination of solubilized compound of formula I with finely dispersed particles of the second fungicidal active ingredient is essential in order to achieve the highest possible fungicidal activity of said preparation.

Surprisingly, it has been found that a fungicidal composition which comprises a compound of formula I, a second fungicidally active ingredient, a polar organic solvent, a solubilizing agent, and a dispersing agent, which has the capability to adsorb irreversibly on the surfaces of hydrophobic particles suspended in water or polar organic solvents, forms a stable suspension of particles of the second fungicidally active ingredient in a solution of the compound of formula I in a liquid mixture of the other components. Further, it has been found that the physical states of the active ingredients are maintained even after these formulations are diluted in water, thus affording sprayable dilutions containing the solubilized compound of formula I and fine particles of the second active ingredient.

Moreover, there is no suggestion in the prior art that such mixtures can advantageously be used for controlling cereal diseases such as *Septoria spp.*.

SUMMARY OF THE INVENTION

The present invention concerns a concentrated liquid fungicidal composition comprising a fungicidally acceptable carrier and (a) at least one compound of formula I, or one of the salts or addition products thereof, which exists in solubilized form;

(b) one or more additional fungicidally active ingredients, which exist as a suspension of fine particles;

(c) a solubilizing agent; and (d) a dispersing agent, which has the capability to adsorb irreversibly on the surfaces of hydrophobic particles suspended in water or polar organic solvents.

Another aspect of the present invention is a concentrated fungicidal composition comprising a fungicidally acceptable carrier and/or surface active agent and synergistically effective amounts of (a) at least one azole derivative of formula I as defined above; and (b) chlorothalonil.

The present invention also includes a method for controlling phytopathogenic fungi which comprises the application of synergistically effective amounts of at least one compound of formula I and chlorothalonil.

DETAILED DESCRIPTION OF THE PREFERRED EMBODIMENTS

Preferred azoles of formula I are those wherein

A represents a nitrogen atom;

R$^1$ and R$^2$ represent a C$_{1-6}$ alkyl group, preferably a methyl group; and R$^3$ is attached in the para-position and represents a fluoro or chloro atom or a C$_{1-6}$ haloalkyl group.

A particularly preferred compound for use in the present invention is metconazole, having the formula IA,

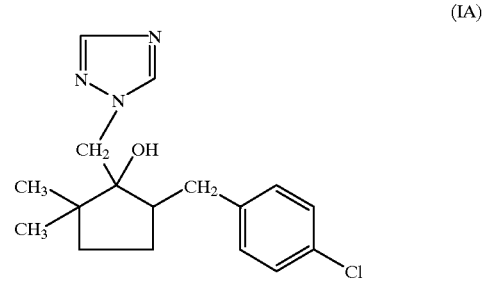

(IA)

which is known from The Pesticide Manual, 10th Edition, The British Crop Protection Council and The Royal Society of Chemistry, 1994, (hereinbelow abbreviated as "Pesticide Manual"), page 669.

The compound of formula I, due to the basic nature of the azole ring, is capable of forming salts or addition products with inorganic or organic acids or metal ions. Examples of inorganic acids which form salts are the hydrohalides such as hydrofluoric acid, hydrochloric acid, hydrobromic acid and hydroiodic acid, and additionally, sulfuric acid, phosphoric acid and nitric acid. Suitable organic acids are those such as formic acid and alkanoic acids such as acetic acid, trifluoroacetic acid, trichloroacetic acid and propionic acid, and additionally, glycolic acid, lactic acid, succinic acid, citric acid, benzoic acid, cinnamic acid, oxalic acid, alkylsulfonic acids, arylsulfonic acids, alkylphosponic acids, arylphosphonic acids, in which the alkyl and aryl moieties are optionally substituted, as for example para-toluenesulfonic acid, salicylic acid, para-phenoxybenzoic acid, 2-acetoxybenzoic acid or the like.

The ions of the metals which represent soft Lewis acids suitable for forming addition products are preferably ions of chromium, manganese, iron, cobalt, nickel, copper, zinc, calcium, magnesium, aluminium, stannum and lead.

However, the active ingredients of formula I and the second fungicidal active ingredient are preferably applied as such.

The second fungicidal compound is, as a rule, a water immiscible organic, in particular, an aromatic solid compound, which has a melting point of at least 60° C., preferably between 70 and 280° C.

The second fungicidal compound can be, for example, one which is capable of combating diseases of cereals (e.g., wheat) such as those caused by Erysiphe Puccinia, Septoria, Gibberella and Helminthosporium spp., seed and soil borne diseases and downy and powdery mildews on vines, early and late blight on solanaceous crops and vegetables, powdery mildew and scab on apples and brassica diseases etc. These mixtures of fungicides provide a broader spectrum of activity than the compound of general formula I alone.

Examples of other fungicidal compounds which can be used in the compositions of the present invention are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds, such as copper oxychloride, and copper sulfate, cycloheximide, cymoxanil, cypofuram, cyproconazole, cyprodinil, dichlofluanid, dichlone, dichloran, diclobutrazol, diclomezine, diethofencarb, difencconazole, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram, in particular chlorothalonil.

Chlorothalonil is the common name of 2,4,5,6-tetrachloro-1,3-benzenedicarbonitrile of formula,

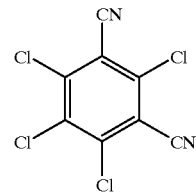

which is described in "The Pesticide Manual", page 193.

The in-tank mixtures of metconazole and chlorothalonil disclosed by U.S. Pat. No. 5,393,770 do not show synergistic effects.

Surprisingly, a strong synergy between azoles of formula I and chlorothalonil in greenhouse trials is found when these compounds are co-formulated and when the activity of these co-formulations is compared with that of the commercial CARAMBA® 60 g/l SL metconazole formulation and with the activity of a commercial DACONIL® 500 g/l SC chlorothalonil formulation. The solo compounds and the co-formulated materials are applied in curative trials to wheat powdery mildew and in protective trials to control wheat Septoria spp. All applications are carried on a per hectare basis with a track sprayer so to simulate practical conditions.

A mixture of fungicides shows synergistic effect if the fungicidal activity of the mixture is larger than the sum of activities of the separately applied compounds (See Colby, S. R., "Calculating synergistic and antagonistic response of herbicide combinations", Weeds 15, pp 20–22 (1967)).

If the actual efficacy (E) exceeds the expected (calculated) one (EE), the mixture displays a synergistic effect.

The compositions of the present invention comprise compounds of formula I and chlorothalonil applied together, in synergistically effective amounts. When so applied, they exhibit an extraordinary efficacy against a broad range of phytopathogenic fungi, in particular against fungi from the classes Ascomycetes, Basidiomycetes, Phycomycetes and Deuteromycetes. They are systemic and may be applied as leaf or soil fungicide.

The mixture according to the invention may be preferably applied for controlling the following phytopathogenic fungal species of the genera: Alternaria, Botrytis, Cercospora, Colletotrichum, Erysiphe (Blumeria), Elsinoe, Fusarium, Gibberella, Guignardia, Helminthosporium, Hemileia, Monilinia, Mycosphaerella, Nectria, Phythium, Phytophthora, Plasmopara, Podosphaera, Pseudocercosporella, Pseudoperonospora, Puccinia, Pyrenophora, Pyricularia, Rhizoctonia, Sclerotinia, Sclerotium, Septoria, Sphaerotheca, Tilletia, Typhula, Uncinula, Uromyces, Ustilago, Venturia, Verticllium and others.

The application rate of the compound of formula I according to this invention is usually in the range of 1 to 500 grams of active ingredient per hectare (g a.i./ha), with rates between 15 to 200 g a.i./ha often achieving satisfactory control. The optimal rate for a specific application will depend on the crop(s) under cultivation and the predominant species of infesting fungus, and may be readily determined by established biological tests known to those skilled in the art.

In general, the preferred application rate of the second fungicidal active ingredient according to this invention, in particular, chlorothalonil, is in the range of 20 to 5,000 g a.i./ha, and preferably is 50 to 1500 g a.i./ha.

The optimal rate for the second fungicidal compound, in particular, chlorothalonil, will, however, depend on the crop(s) under cultivation and the level of infestation by the fungus, and can readily be determined by established biological tests.

The ratio (by weight) of the compound of formula I to the second fungicidal compound, in particular, chlorothalonil, is as a rule, from 1:200 to 2:1. The preferred ratio formula I: chlorothalonil may vary, e.g., from about 1:100 to about 1:1, in particular from about 1:20 to about 1:5.

The active compounds will be formulated together in a suitable ratio according to the present invention, together with usual carriers.

The fungicidally acceptable carriers are liquid carriers, preferably water miscible or partially water miscible organic solvents or a mixture thereof with water. Mixtures of water miscible solvents and water are preferred. In a preferred embodiment of the present invention, the weight ratio of the water miscible solvent to water is in the range of from 1:5 to 5:1, preferably from 1:2 to 2:1, in particular from 1:1.25 to 1.25 to 1.

Water-miscible or partially water-miscible organic solvents may be alcohols and glycols as well as their ethers and esters, e.g. ethanol, propanol, butanol, pentanol, benzylalcohol, ethylene glycol, propylene glycol, ketones such as methylethylketone or cyclohexanone, strongly polar solvents, preferably 1-alkyl pyrrolidones such as N-methyl-2-pyrrolidone, N-n-octyl-2-pyrrolidone or N-cyclohexyl-2-pyrrolidone, or lactones such as γ-butyrolactone, in particular propylene glycol. Mixtures of different water-miscible or partially water-miscible organic solvents are often suitable.

The solubilizing agent is a surfactant preferably from the group of alkoxylates of aliphatic alcohols. A preferred alkoxylate of an aliphatic alcohol is based on alkoxy units having 2 carbon atoms, thus being a mixed ethoxylate or 2 and 3 carbon atoms, thus being a mixed ethoxylate/propoxylate. In a preferred aliphatic alcohol alkoxylate, the alkoxylate chain may have at least 5 alkoxy moieties, suitably from 5 to 25 alkoxy moities, preferably 5 to 15, in particular 5 to 9. The alcohol moiety is, as a rule, derived from a $C_{9-18}$ aliphatic alcohol. Preferred alcohols are at least 50% by weight at primary and at least 50% by weight straight chain alcohols and with at least 50% by weight having one hydroxy group.

Particularly preferred solubilizing agents are those such as NEODOL® (formerly DOBANOL®) alcohol ethoxylates from Shell Chemical Co. Ltd. In a preferred embodiment of the present invention, the weight ratio of the solubilizing agent to the compound of formula I is in the range of from 5:1 to 20:1, preferably from 5:1 to 15:1.

The dispersing agent, which has the capability to adsorb irreversibly on the surfaces of hydrophobic particles suspended in water or polar organic solvents, is preferably selected from the group of polymeric surfactants, preferably surface active acrylic graft copolymers (such as those sold under the tradename ATLOX®) or from the group of polymeric naphthalene sulfonates. Additional dispersing agents such as the potassium salts of polyaryl alkoxylate phosphate esters (sold under the tradename SOPROPHOR®) can also be utilized.

In a preferred embodiment of the present invention the weight ratio of the dispersing agent to the additional fungicidal active ingredient is in the range of from 1:50 to 1:300, preferably from 1:100 to 1:150.

Preferred are liquid formulations, which comprise the following constituents:

a water miscible organic solvent or a mixture of such a solvent with water; and an azole derivative of formula I, in particular metconazole;

at least one second fungicidally active ingredient; in particular chlorothalonil, a solubilizing agent, e.g., an alkoxylate of an aliphatic alcohol being an ethoxylate or a mixed ethoxylate/propoxylate composed of 5 to 25 alkoxy moieties, in particular NEODOL® alcohol ethoxylates, (commercially available from Shell Chemical Co. Ltd.); and one or more dispersing agents, which have the capability to adsorb irreversibly on the surfaces of hydrophobic particles suspended in water or polar organic solvents, preferably selected from the group of surface active acrylic graft copolymers, such as ATLOX® 4913 (commercially available from ICI Surfactants), and polymeric naphthalene sulfonates, such as SUPRAGIL® MNS 90 (commercially available from Rhodia, formerly Rhone-Poulenc); and a foam breaking agent, in particular a mixture of perfluoroalkyphosphonic acids and/or perfluoroalkylphosphinic acids, in particular, Defoamer® SF or Fluowett® PL 80, (commercially available from Clariant GmbH).

In a preferred embodiment of this invention, the liquid co-formulation consists essentially of 0.5 to 10%, preferably 1 to 7%, by weight of an azole derivative of formula I;

15 to 60%, preferably 20 to 40%, by weight of at least one second fungicidally active ingredient;

10 to 50%, preferably 15 to 35% by weight of a solubilizing agent, 0.1 to 5%, preferably 0.2 to 2%, by weight of one or more dispersing agents, one of which has the capability to adsorb irreversibly on the surfaces of hydrophobic particles suspended in water or polar organic solvents, 0.1 to 5%, preferably 0.5 to 2.5%, by weight a foam breaking agent;

5 to 35%, preferably 15 to 30%, by weight of a water miscible or partially water miscible organic solvent or a mixture thereof with water;

0.01 to 0.5% by weight of a preservative; and 0.05 to 1%, in particular 0.1 to 0.6%, by weight of a structuring agent; and the sum of all ingredients in the composition is 100%.

In a preferred embodiment of the present invention, the mean particle size of the component (b), in particular, chlorothalonil, contained in the formulation is less than 3.0 µm, preferably 1.3 to 2.7 µm, in particular 1.5 to 2.5 µm. Typically, such sizing is accomplished using conventional milling apparatus.

The formulations of the present invention represent a stable suspension of particles of the second fungicidally active ingredient, in particular, chlorothalonil, in a solution of the compound of formula I, in particular, metconazole, in a liquid mixture of the other components. The sedimentation behavior of the formulations according to the present invention upon storage under practical condition is acceptable. The physical states of the active ingredients are maintained after these formulations are diluted in water, i.e., the resultant spray dilutions contain solubilized metconazole and fine particles of chlorothalonil without interfering phase separation. The combination of solubilized metconazole and finely dispersed particles of chlorothalonil is essential in order to achieve the highest possible fungicidal activity of said preparation.

A method of preparing such a composition is also provided which comprises bringing a compound of formula I and a second fungicidal active ingredient, in particular, chlorothalonil, as defined above, into association with at least one carrier. It is also envisaged that different isomers or mixtures of isomers may have different levels or spectra of activity and thus compositions may comprise individual isomers or mixtures of isomers.

A composition according to the invention preferably contains from 0.5% to 95%, preferably 15% to 70%, in particular 25% to 50%, by weight (w/w) of the active ingredients.

The carrier in a composition according to the invention is any material with which the active ingredient is formulated to facilitate application to the locus to be treated, which may, for example, be a plant, seed or soil, or to facilitate storage, transport or handling. The carrier may be a solid or a liquid, preferably a liquid, but may include material which is normally a gas but which has been compressed to form a liquid.

The compositions may be manufactured into the liquid concentrates, by well-established procedures. These procedures include intensive mixing and/or milling of the active ingredients with other substances, such as solvents, surface active compounds (surfactants), and optionally solid and/or liquid auxiliaries and/or adjuvants. The form of application such as spraying, atomizing dispersing or pouring may be chosen like the compositions according to the desired objectives and the given circumstances.

Pesticidal compositions are often formulated and transported in a concentrated form which is subsequently diluted by the user before application. The presence of small amounts of a carrier which is a surfactant facilitates this process of dilution. Thus, preferably at least one compound of the carrier in a composition according to the invention is a surfactant. For example, the composition may contain at two or more carriers, at least one of which is a surfactant. Surfactants may be nonionic, anionic, cationic or zwitterionic substances with good dispersing, emulsifying and wetting properties depending on the nature of the compound according to general formula I to be formulated. Surfactants may also be mixtures of individual surfactants.

The compositions of the invention may also contain other additives such as defoamers, preservatives, corrosion inhibitors, stabilizers, structuring agents, penetrants and stickers, and water or an organic liquid in which the active ingredient is substantially insoluble; certain organic solids or inorganic salts may be present dissolved in the formulation to assist in preventing sedimentation and crystalization or as antifreeze agents for water. Suitable preservatives include the antimicrobial sodium 1,2-benzisothiazolin-3-one, sold under the tradename Proxel®. Suitable structuring agents are clays, such as the attapalgite clays sold under the Attagel® tradename.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

Formulation A

| Component | Function | Concentration |
| --- | --- | --- |
| Metconazole | Active Ingredient | 30 g/l |
| Chlorothalonil | Active Ingredient | 375 g/l |
| Atlox ® 4913[1] | Dispersing Agent | 3 g/l |
| NEODOL ® 91-6[2] | Solubilizer | 300 g/l |
| Soprophor ® FLK[3] | Dispersing Agent | 12 g/l |
| Defoamer ® SF[4] | Defoamer | 20 g/l |
| Proxel ® GXL[5] | Preservative | 0.5 g/l |
| Attagel ® 50[6] | Structuring Agent | 2 g/l |
| Propylene glycol | Solvent | 120 g/l |
| Water | Continuous Phase | to 1 l |

Formulation A is prepared by dissolving metconazole in propylene glycol and Neodol 91-6 (pre-mix I), mixing together the other ingredients with a high shear mixer (pre-mix II) and mixing together pre-mix I and pre-mix II.

Formulation B

| Component | Function | Concentration |
| --- | --- | --- |
| Metconazole | Active Ingredient | 30 g/l |
| Chlorothalonil | Active Ingredient | 375 g/l |
| Atlox ® 4913[1] | Dispersing Agent | 3 g/l |
| NEODOL ® 91-6[2] | Solubilizer | 300 g/l |
| Soprophor ® FLK[3] | Dispersing Agent | 12 g/l |
| Defoamer ® SF[4] | Defoamer | 30 g/l |
| Proxel ® GXL[5] | Preservative | 0.5 g/l |
| Attagel ® 50[6] | Structuring Agent | 5 g/l |
| Propylene glycol | Solvent | 120 g/l |
| Water | Continuous Phase | to 1 l |

Formulation B is prepared by dissolving metconazole in propylene glycol and Neodol 91-6 (pre-mix I), mixing together the other ingredients with a high shear mixer, subsequently reducing the particle size of chlorothalonil by bead milling to a mean particle size of 1.5–2.5 $\mu$m (pre-mix II) and mixing together pre-mix I and pre-mix II.

Formulation C

| Component | Function | Concentration |
| --- | --- | --- |
| Metconazole | Active Ingredient | 30 g/l |
| Chlorothalonil | Active Ingredient | 375 g/l |
| Supragil ® MNS 90[3] | Dispersing Agent | 10 g/l |
| NEODOL ® 91-6[2] | Solubilizer | 300 g/l |
| Defoamer ® SF[4] | Defoamer | 20 g/l |
| Proxel ® GXL[5] | Preservative | 0.5 g/l |
| Attagel ® 50[6] | Structuring Agent | 2 g/l |
| Propylene glycol | Solvent | 120 g/l |
| Water | Continuous Phase | to 1 l |

Formulation C is prepared as Formulation A.

The components of the formulations A, B and C are available from the following sources:

1) available from ICI Surfactants
2) available from Shell Chemical CO., Ltd.

3) available from Rhodia 4) available from Clariant GmbH 5) available from Zeneca 6) available from Engelhard Corp.

The phase separation of the formulations A and B has been examined as follows:

The formulation have been stored 8 weeks at different temperatures or at a temperature cycle between 0 and 35° C. (0/35), respectively. The supernatant liquid (s.l.) has been assessed visually, and reported as a volume percentage. The sediment (sed.) has been assessed by the careful introduction of a glass rod into the container and found to be moderate (mo) or in traces (tr) only. The results of this assessment is given in the following table I.

TABLE I

| Formulation | | Phase separation | | | |
| --- | --- | --- | --- | --- | --- |
| | | Storage Temperature (° C.) | | | |
| | | 20 | 28 | 37 | 0/35 |
| A | s.l. | 25% | 29% | 38% | 27% |
| B | s.l. | 6% | 11% | 15% | 13% |
| A | sed. | m | m | m | m |
| B | sed. | tr | tr | tr | tr |

As commodity the compositions according to the present invention are in a concentrated form whereas the end-user generally employs diluted compositions. The compositions may be diluted to a concentration of 0.001% of active ingredients.

The following examples illustrate specific embodiments of the present invention; however, the invention is not limited to the embodiments so illustrated, but includes the entire scope of the appended claims.

EXAMPLES

Effect of CARAMBA® (60 g/l metconazole), DACONIL® (500 g/l chlorothalonil), and a metconazole/chlorothalonil 30/375 g/l SC co-formulations (Formulation C) against cereal diseases.

Example 1

Efficacy (% control in bold) of CARAMBA and DACONIL at various dose rates in comparison to rates of the metconazole/chlorothalonil co-formulation (Formulation C) against wheat Septoria nodorum in a 3 days residual test (sprayed with an even-spray-nozzle in a track sprayer).

Evaluation

Evaluation was (carried out by assessing the percentage of infected leaf area of each of the 4 replicates. The activity in % was calculated using the ABBOTT formula:

$$\% \text{ activity} = 100 - \frac{\% \text{ infection in treated}}{\% \text{ infection in untreated}} \times 100$$

The results are shown in Table II, in which the experimental efficacy is given in bold figures and the expected value is given in brackets in italic figures:

TABLE II

| Dose of Chlorothalonil | Metconazole (g ai/ha) | | | | | |
| --- | --- | --- | --- | --- | --- | --- |
| (g ai/ha) | 0 | 3.8 | 5.6 | 7.5 | 11.3 | 15 | 22.5 |
| 0 | | | 0 | | 0 | | 9 |
| 47 | | 29 | | | | | |
| 69 | 0 | | (0) | | | | |
| 94 | | | | 70 | | | |
| 138 | 0 | | | | (0) | | |
| 188 | | | | | | 71 | |
| 275 | 0 | | | | | | (9) |

It is clear from the results that, against wheat Septoria nodorum, both the solo products were inactive at the tested dose rates whereas the co-formulation had efficacies of 29–71% control in the dose range tested which suggests strong synergy.

Example 2

Efficacy (% control in bold) of CARAMBA and DACONIL at various dose rates in comparison to rates of the co-formulated metconazole/chlorothalonil 30/375 g/l SC (Formulation C) against wheat powdery mildew in a 2 days curative test (sprayed with an even-spray-nozzle in a track sprayer).

The results are shown in Table III, in which the experimental efficacy is given in bold figures and the expected value is given in brackets in italic figures:

TABLE III

| Dose of Chlorothalonil | Metconazole (g ai/ha) | | | | | | | |
| --- | --- | --- | --- | --- | --- | --- | --- | --- |
| (g ai/ha) | 0 | 0.9 | 1.4 | 1.9 | 2.8 | 3.8 | 5.6 | 7.5 | 11.3 |
| 0 | | | 0 | | 18 | | 70 | | 100 |
| 12 | | 42 | | | | | | | |
| 17 | 0 | | (0) | | | | | | |
| 23 | | | | 67 | | | | | |
| 34 | 0 | | | | (18) | | | | |
| 47 | | | | | | 95 | | | |
| 69 | 0 | | | | | | (70) | | |
| 94 | | | | | | | | 100 | |
| 138 | 0 | | | | | | | | (100) |

What is claimed is:

1. A concentrated liquid fungicidal composition comprising a fungicidally acceptable water miscible or partially water miscible, organic solvent or mixture thereof with water carrier and
   (a) from about 0.5 to about 10% by weight of at least one compound of formula I,

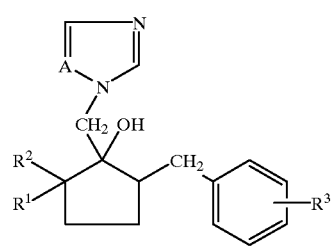

(I)

in which

R¹ and R² each independently represent hydrogen atom or an optionally substituted alkyl, alkenyl, alkynyl or alkadienyl group;

R³ represents a halogen atom or an optionally substituted alkyl, alkenyl, alkynyl, alkadienyl, alkoxy or aryl group; and A represents a nitrogen atom or a CH group;

or one of the salts or addition products thereof, which exists in solubilized form;

(b) from 15 to 60% by weight of one or more additional fungicidally active ingredients, which exist as a suspension of fine particles;

(c) from about 10 to about 50% by weight of a solubilizing agent; and which are alkoxylates of aliphatic alcohols (d) from about 0.1 to about 5% by weight of one or more dispersing agent, which has the capability to adsorb irreversibly on the surfaces of hydrophobic particles suspended in water or polar organic solvents and which is selected from the group consisting of polymeric surfactants and potassium salts of polyaryl alkoxylate phosphate esters.

2. A composition according to claim 1, wherein the compound of formula I is metconazole.

3. A composition according to claim 1, wherein the ratio (by weight) of the compound of formula I (a) to the additional fungicidally active ingredient (b) is from 1:200 to 2:1.

4. A composition according to claim 3, wherein the ratio (by weight) of the compound of formula I (a) to the additional fungicidally active ingredient (b) is from 1:20 to 1:5.

5. A composition according to claim 1, wherein the additional fungicidally active ingredient (b) is a water immiscible organic compound, which has a melting point of at least 60° C.

6. A composition according to claim 5, wherein said additional fungicidally active ingredient has a mean particle size of less than 3.0 μm.

7. A composition according to claim 6, wherein said additional fungicidal active ingredient has a mean particle size of 1.5 to 2.5 μm.

8. A composition according to claim 5, wherein the additional fungicidally active ingredient is chlorothalonil.

9. A composition according to claim 1, wherein the dispersing agents are selected from the group consisting essentially of surface active acrylic graft copolymers or polymeric naphthalene sulfonates; and which additionally includes a foam breaking agent.

10. A composition according to claim 9, wherein the foam breaking agent is a mixture of perfluoroalkyphosphonic acids and/or perfluoroalkylphosphinic acids.

11. A composition according to claim 9, which consists essentially of 0.5 to 10% by weight of a compound derivative of formula I;

15 to 60% by weight of at least one second fungicidally active ingredient;

10 to 50% by weight of a solubilizing agent, 0.1 to 5% by weight of one or more dispersing agents, one of which has the capability to adsorb irreversibly on the surfaces of hydrophobic particles suspended in water or polar organic solvents, 0.1 to 5% by weight a foam breaking agent;

5 to 35% by weight of a water miscible or partially water miscible organic solvent or a mixture thereof with water;

0.01 to 0.5% by weight of a preservative; and 0.05 to 1% by weight of a structuring agent.

12. A method of controlling the growth of fungi at a locus which comprises diluting a concentrated composition according to claim 1 with water and applying said diluted composition to the locus.

13. A method of controlling the growth of fungi at a locus which comprises diluting a concentrated composition according to claim 3 with water and applying said diluted composition to the locus.

14. A method of controlling the growth of wheat Septoria spp. or wheat powdery mildew at a locus which comprises diluting a concentrated composition according to claim 1 with water and applying said diluted composition to the locus.

15. A method of controlling the growth of wheat Septoria spp. or wheat powdery mildew at a locus which comprises diluting a concentrated composition according to claim 3 with water and applying said diluted composition to the locus.

* * * * *